(12) United States Patent
DeJovin et al.

(10) Patent No.: US 8,440,688 B2
(45) Date of Patent: May 14, 2013

(54) COMPOUNDS, FORMULATIONS AND METHODS FOR REDUCING SKIN WRINKLES, CREASING AND SAGGING

(75) Inventors: Jack DeJovin, New Brunswick, NJ (US); Isabelle Jean DeJovin, New Brunswick, NJ (US)

(73) Assignee: Galderma Laboratories Inc., Fort Worth, TX (US)

( * ) Notice: Subject to any disclaimer, the term of this patent is extended or adjusted under 35 U.S.C. 154(b) by 0 days.

(21) Appl. No.: 13/196,333

(22) Filed: Aug. 2, 2011

(65) Prior Publication Data

US 2011/0286945 A1 Nov. 24, 2011

Related U.S. Application Data

(63) Continuation of application No. 12/180,790, filed on Jul. 28, 2008, now abandoned.

(60) Provisional application No. 60/952,298, filed on Jul. 27, 2007.

(51) Int. Cl.
*A01N 43/42* (2006.01)

(52) U.S. Cl.
USPC .......................... 514/293; 514/844; 424/401

(58) Field of Classification Search .................. 424/401; 514/293, 844
See application file for complete search history.

(56) References Cited

U.S. PATENT DOCUMENTS

| | | | |
|---|---|---|---|
| 5,254,331 A * | 10/1993 | Mausner | 424/59 |
| 5,989,528 A | 11/1999 | Tanner et al. | |
| 6,444,647 B1 | 9/2002 | Robinson et al. | |
| 7,252,816 B1 * | 8/2007 | Angel et al. | 424/59 |
| 2005/0020600 A1 | 1/2005 | Scherer | |
| 2006/0057081 A1 * | 3/2006 | Boxrud | 424/59 |
| 2006/0216251 A1 | 9/2006 | Morariu | |
| 2006/0264515 A1 | 11/2006 | Dejovin et al. | |
| 2006/0275228 A1 | 12/2006 | Bissett et al. | |
| 2007/0082070 A1 | 4/2007 | Stookey et al. | |

FOREIGN PATENT DOCUMENTS

| | | |
|---|---|---|
| DE | 29612123 | 9/1996 |
| EP | 1090630 | 4/2001 |
| JP | 2004196759 A * | 7/2004 |
| WO | WO9100088 | 1/1991 |
| WO | WO9633709 | 10/1996 |
| WO | WO-2005/002580 A1 * | 1/2005 |
| WO | WO2009017705 | 2/2009 |

OTHER PUBLICATIONS

Morissette Guillaume et al., "Anti-wrinkle properties of aminies: vacuolar cytopathology medicated by the V-ATPase" M/A Medicine Sciences, Soociete Des Periodiques Flammarion, Paris, FR, vol. 23, No. 6-7, Jun. 1, 2007, pp. 579-580. O miroir, dis-moi comment les amines effacent les rides , XP00913897.

\* cited by examiner

*Primary Examiner* — Ali Soroush
(74) *Attorney, Agent, or Firm* — Hoffmann & Baron, LLP

(57) ABSTRACT

Methods, compounds, and topical formulations for reduction of skin sagging, creasing and/or wrinkling are disclosed. The methods comprise topically applying a composition comprising an α2 adrenergic receptor agonist. Amelioration of skin sagging, creasing and/or wrinkling begins within minutes after topical application of a disclosed composition. A single application can significantly reduce skin sagging, creasing and/or wrinkling for at least about 8 hours.

15 Claims, No Drawings

COMPOUNDS, FORMULATIONS AND METHODS FOR REDUCING SKIN WRINKLES, CREASING AND SAGGING

CROSS-REFERENCE TO RELATED APPLICATIONS

This application is a continuation of U.S. application Ser. No. 12/180,790 filed Jul. 28, 2008, which claims priority to U.S. Patent Application Ser. No. 60/952,298 filed Jul. 27, 2007, which is incorporated by reference herein in its entirety.

The present teachings are directed to compounds and methods for treatment or prevention of skin wrinkles and sagging.

BACKGROUND OF THE INVENTION

Skin wrinkles, creasing and sagging are common and generally undesirable. Such skin conditions can result from many causes, such as aging.

Many different treatments are used to reverse wrinkles, creasing or skin sagging. Examples of these treatments include injection of toxins such as botulinum toxin; injection of fillers such as collagen, fat, and hyaluronic acid, topical formulations of tretinoin, chemical peeling, dermabrasion, laser resurfacing, microdermabrasion, photorejuvenation, and plastic surgery such as face-lifts and forehead lifts. All of these procedures have associated side effects and/or cautions (see, e.g., the web site www.mayoclinic.com/health/wrinkle-treatment/SN00008)

Thus, there remains a need for compositions and methods for reducing skin wrinkles, creasing and sagging.

SUMMARY OF THE INVENTION

The present inventors have developed topical skin formulations and methods for reducing skin wrinkles, creasing and sagging. Compositions of the invention comprise α2 adrenergic receptor agonists, which have a skin-tightening effect and ameliorate skin wrinkles, skin creasing, skin sagging or all. These compounds can be delivered in topical skin compositions that promote effectiveness of the compound in amounts effective for ameliorating skin wrinkles, creasing and sagging without inducing intolerable side effects, including systemic side effects.

Accordingly, in various aspects, the present teachings disclose methods of reducing skin wrinkling, creasing and sagging. In various configurations, these methods comprise topically administering to the skin of a person such as a patient in need of treatment a composition comprising an active ingredient selected from at least one $\alpha_2$ adrenergic receptor agonist, a pharmaceutically acceptable salt thereof and a combination thereof.

In various aspects, a composition is administered in an amount effective for amelioration of skin wrinkles, creasing and sagging. An amount effective for amelioration of skin wrinkles, creasing and sagging is any amount that is locally effective for amelioration of skin wrinkles, creasing and sagging upon topical administration.

No special preparation of the skin is required prior to administration of a composition, although cleaning of the skin prior to administration can enhance effectiveness. In addition, various formulations can be non-restrictive with regard to other skin care and cosmetic products. Application of a formulation comprising an $\alpha_2$ adrenergic receptor agonist can be compatible with, e.g., separate application of make-up.

Furthermore, in some configurations, a skin care or cosmetic product can comprise an $\alpha_2$ adrenergic receptor agonist, so that the user can simultaneously receive, e.g., the benefits of both skin-tightening effects and masking effects by application of a single product to the skin.

In various configurations, an $\alpha_2$ adrenergic receptor agonist can have the structure of a compound shown below:

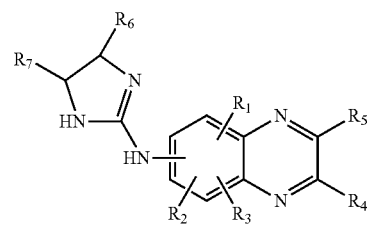

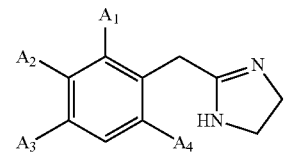

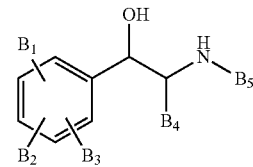

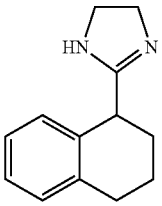

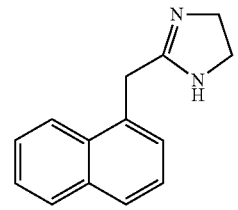

wherein each of $R_1$, $R_2$, and $R_3$ is independently hydrogen, halogen, alkyl, or alkoxy; each of $R_4$ and $R_5$ is independently hydrogen, alkyl, or alkoxy; and each of $R_6$ and $R_7$ is independently hydrogen, nitro, alkyl, or alkoxy; wherein each of $A_1$, $A_3$, and $A_4$ is independently hydrogen or alkyl; and $A_2$ is independently hydrogen or hydroxy; and wherein each of $B_1$, $B_2$, and $B_3$ is independently hydrogen, hydroxy, or alkoxy; and each of $B_4$ and $B_5$ is independently hydrogen or alkyl. Accordingly, an $\alpha_2$ adrenergic receptor agonist can be brimonidine, naphazoline, tetrahydrozaline, oxymetazoline, xylometazoline, epinephrine, norepinephrine, phenylephrine, and methoxamine. In some embodiments, an $\alpha_2$ adrenergic receptor agonist can be a reversible $\alpha_2$ adrenergic receptor agonist.

In various embodiments, a composition of the present teachings comprising an $\alpha_2$ adrenergic receptor agonist can further comprise a pharmaceutically acceptable carrier. In some aspects, a composition can be a spray, a mist, an aerosol, a lotion, a foam, a gel, a cream, an ointment, a paste, an unguent, an emulsion, a liposomal suspension, a colloid or a combination thereof, while in other aspects, a composition can be formulated as a cosmetic, a foundation, a moisturizer, a sun-blocking agent.

In some configurations, a composition can further comprise a pharmaceutically acceptable carrier, which can comprise an aqueous gel comprising water and a water-gelling amount of a pharmaceutically acceptable gelling agent selected from a carbomer, a glycerine polyacrylate, and a mixture thereof, and can be a spray, a mist, an aerosol, a lotion, a foam, a gel, a cream, an ointment, a paste, an unguent, an emulsion, a liposomal suspension, a colloid or a combination thereof. A cream or an ointment can comprise stearic acid, stearyl alcohol, cetyl alcohol, glycerin, and/or water.

In various configurations, a topical composition can comprise an $\alpha_2$ adrenergic receptor agonist, a pharmaceutically acceptable salt or a combination thereof in an amount from at least about 0.01% w/w up to about 5% w/w, and furthermore, a composition can have a pH of from about 5 to about 8. In various aspects, compositions of the present teachings can further comprise a preservative, a local anesthetic, and/or a skin humectant.

In some embodiments, a topical composition for reducing skin wrinkles, creasing and/or sagging, hereinafter referred to as "skin tightening," can comprise at least one first active ingredient selected from an $\alpha_2$ adrenergic receptor agonist, a pharmaceutically acceptable salt thereof and a combination thereof, and at least one second active pharmaceutical ingredient selected from azelaic acid, benzoyl peroxide, isotretinoin, an antibiotic, a chemically modified antibiotic, a pharmaceutically acceptable salt thereof and a combination thereof. In some configurations, an antibiotic can be clindamycin, doxycycline, erythromycin, metronidazole, sulfacetamide, tetracycline, or a combination thereof. A topical composition can comprise the first active ingredient in a prescription strength concentration or in an over-the-counter strength concentration. In some configurations of methods of the present teachings, an antibiotic or a chemically modified antibiotic can be administered in an amount effective for treatment of skin sagging, creasing and/or wrinkling.

The symptoms that can be ameliorated include symptoms such as, for example, skin wrinkling, skin creasing, and skin sagging.

In various aspects of the present teachings, an amount of a composition effective for skin tightening can be an amount which begins to provide skin tightening effects within about 5 minutes after the administering. In various other aspect, an amount effective for skin tightening can be an amount which reduces skin wrinkling, creasing or sagging for at least about 8 hours, for up to about 12 hours, for up to about 18 hours, or for up to about 24 hours.

In certain aspects of the present teachings, the present inventors have developed pharmaceutical packages for ameliorating skin sagging, creasing and/or wrinkling A package according to these aspects can comprise a first active ingredient selected from at least one $\alpha_2$ adrenergic receptor agonist, a pharmaceutically acceptable salt thereof and a combination thereof, in an amount effective for amelioration of skin sagging, creasing and/or wrinkling A package can further a second active pharmaceutical ingredient selected from azelaic acid, benzoyl peroxide, isotretinoin, an antibiotic, a chemically modified antibiotic, a pharmaceutically acceptable salt thereof and a combination thereof, and furthermore can comprise a pharmaceutically acceptable carrier, a container, and instructions for use of the topical composition.

In some configurations, methods of reducing skin sagging, creasing and/or wrinkling can comprise selecting a first active ingredient on the basis of it's having $\alpha_2$ adrenergic receptor agonist activity, and topically administering to the skin of an individual such as a patient in need of treatment a composition comprising an active ingredient selected from at least one $\alpha_2$ adrenergic receptor agonist, a pharmaceutically acceptable salt thereof and a combination thereof, in an amount effective for reduction of skin sagging, creasing and/or wrinkling. In other configurations, methods of reducing skin sagging, creasing and/or wrinkling can comprise selecting the active ingredient on the basis of it's having ameliorating activity for skin sagging, creasing and/or wrinkling, or on the basis of having both $\alpha_2$ adrenergic receptor agonist activity and ameliorating activity for skin sagging, creasing and/or wrinkling.

DETAILED DESCRIPTION

The present inventors have discovered compounds, compositions, formulations, and methods for reducing skin sagging, creasing and/or wrinkling. The methods comprise topically administering to the skin a composition or formulation comprising an $\alpha_2$ adrenergic receptor agonist.

$\alpha_2$ adrenergic receptor agonists of the present teachings are listed in Table 1 below.

TABLE 1

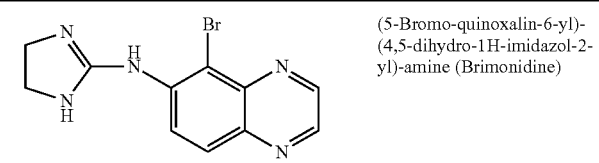

(5-Bromo-quinoxalin-6-yl)-(4,5-dihydro-1H-imidazol-2-yl)-amine (Brimonidine)

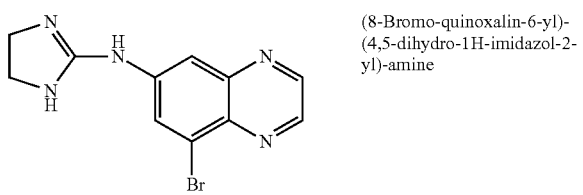

(8-Bromo-quinoxalin-6-yl)-(4,5-dihydro-1H-imidazol-2-yl)-amine

TABLE 1-continued

| Structure | Name |
|---|---|
| 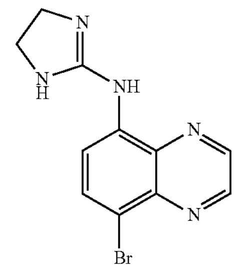 [SMILES: Brc1ccc(NC2=NCCN2)c2nccnc12] | (8-Bromo-quinoxalin-5-yl)-(4,5-dihydro-1H-imidazol-2-yl)-amine |
| 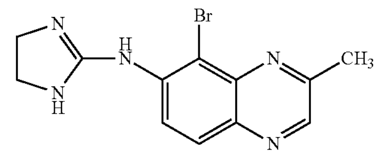 [SMILES: Cc1cnc2ccc(NC3=NCCN3)c(Br)c2n1] | (5-Bromo-3-methyl-quinoxalin-6-yl)-(4,5-dihydro-1H-imidazol-2-yl)-amine |
| 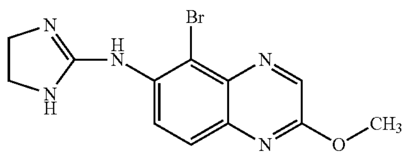 [SMILES: COc1cnc2c(Br)c(NC3=NCCN3)ccc2n1] | (5-Bromo-2-methoxy-quinoxalin-6-yl)-(4,5-dihydro-1H-imidazol-2-yl)-amine |
| 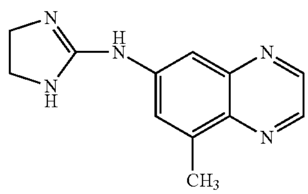 [SMILES: Cc1cc(NC2=NCCN2)cc2nccnc12] | (4,5-dihydro-1H-imidazol-2-yl)-(8-methyl-quinoxalin-6-yl)-amine |
| 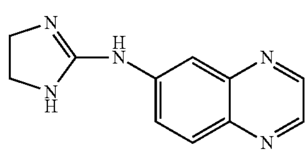 [SMILES: c1cnc2cc(NC3=NCCN3)ccc2n1] | (4,5-dihydro-1H-imidazol-2-yl)-quinoxalin-6-yl-amine |
| 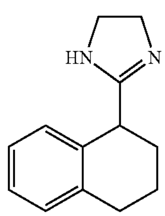 [SMILES: c1ccc2c(c1)CCCC2C1=NCCN1] | Tetrahydrozaline |
| 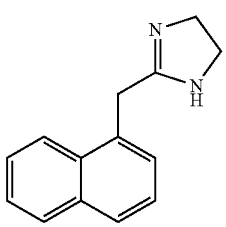 [SMILES: c1ccc2c(CC3=NCCN3)cccc2c1] | Naphazoline |
| 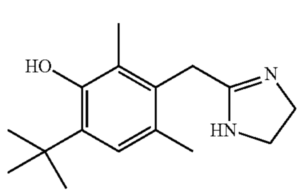 [SMILES: Cc1cc(C(C)(C)C)c(O)c(C)c1CC1=NCCN1] | Oxymetazoline |

TABLE 1-continued

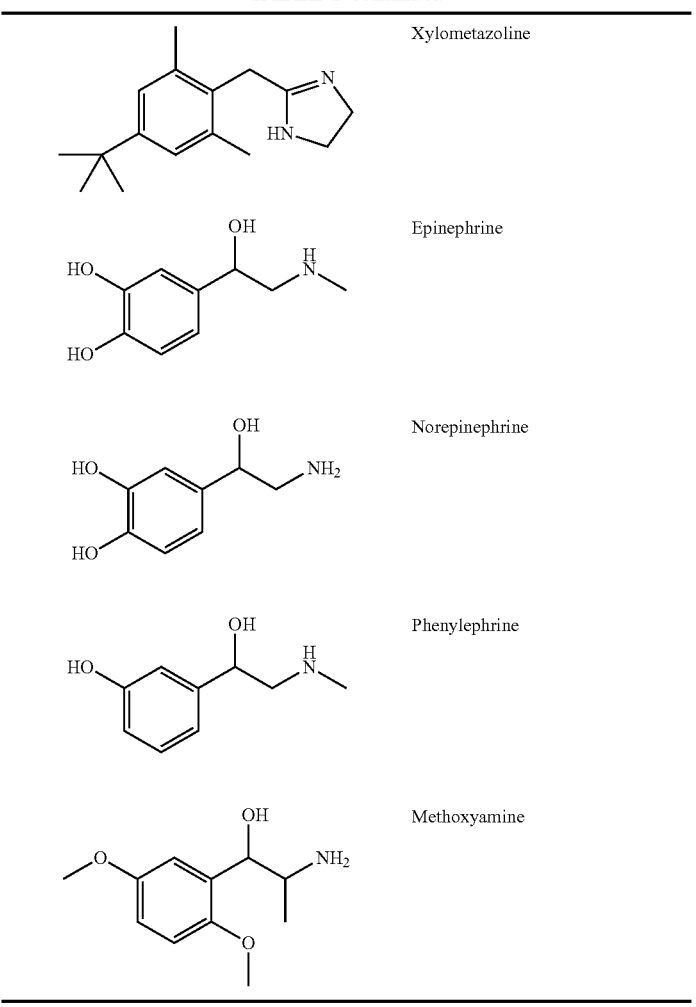

| | |
|---|---|
| | Xylometazoline |
| | Epinephrine |
| | Norepinephrine |
| | Phenylephrine |
| | Methoxyamine |

Compounds of the present compositions and used in the present methods are well known in the art as $\alpha_2$ adrenergic receptor agonists, and have powerful vasoconstricting effects when introduced into the body of mammals, particularly humans. Compounds according to the teachings of the present invention may also include pharmaceutically acceptable salts of the compounds described herein, analogs thereof, prodrugs thereof and combinations of same.

The compounds of the present teachings can be prepared in accordance with well-known synthetic procedures, for example, using the general synthetic procedures set forth in U.S. Pat. No. 3,890,319 (issued Jun. 17, 1975) and U.S. Pat. No. 4,029,792 (issued Jun. 14, 1977) both of which are hereby incorporated herein by reference. Scheme 1 below illustrates one method to synthesize compounds of Formula I Scheme 1

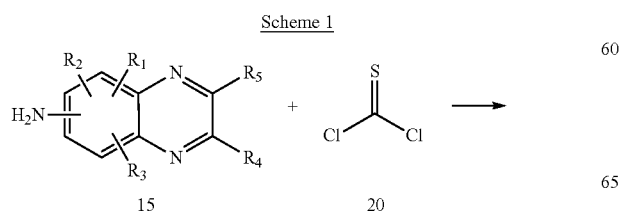

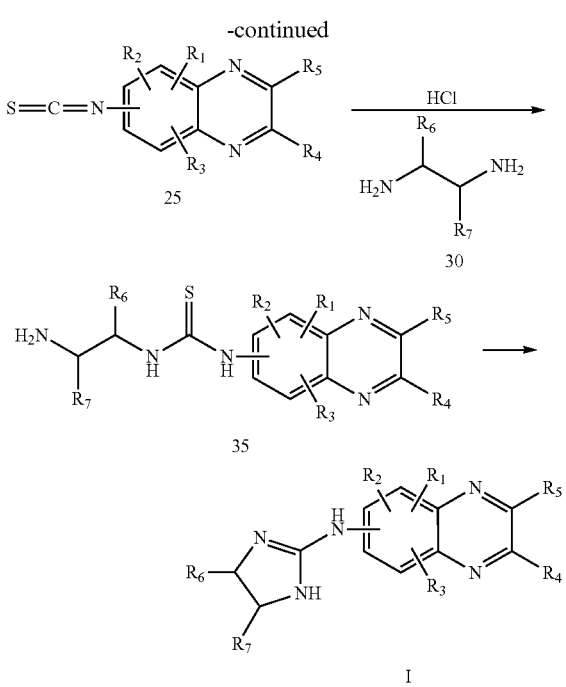

Compounds of the invention can be synthesized by reaction of the appropriate quinoxalines 15 with thiophosgene 20 to form corresponding isothiocyanates 25. The reaction with thiophosgene can be carried out in aqueous solution or in dilute aqueous hydrochloric acid at room temperature in a period of about 2 hours. Alternatively, the thiophosgene 20 dissolved in a water-immiscible solvent, such as chloroform, can be added to a basic aqueous solution (sodium carbonate) of quinoxalines 15 and stirred for about two hours. In the first alternative, isothiocyanates 25 precipitate from the reaction mixture. Precipitation can be completed by neutralization with excess aqueous base. Precipitated isothiocyanates 25 can be recovered by filtration and dissolved in a suitable solvent, e.g., chloroform, to form a solution. The solution can be dried (e.g., over $MgSO_4$), filtered, and concentrated to yield the isothiocyanates 25.

Isothiocyanates 25 can be treated with an excess of the appropriately substituted ethylene diamine to form the corresponding 3-quinoxalin-6-yl-thioureas 35. Isothiocyanates 25 can be reacted with an excess (e.g., 5 moles to 1 mole) of ethylene diamine 30 in a suitable solvent, e.g., diethyl ether, benzene, chloroform or dioxane. The reaction can be carried out at room temperature for about 2 hours. 3-Quinoxalin-6-yl-thioureas 35 precipitate and can be recovered by filtration and washing the filter cake with solvent.

Cyclization of 3-quinoxalin-6-yl-thioureas 35 to afford compounds of the invention 10 can be effected by heating a suspension of thioureas 35 with mercuric or cupric oxide in a suitable organic solvent, e.g., ethanol. The mercuric or cupric oxide can be replaced by an organic soluble mercuric or cupric salt, e.g., mercuric or cupric acetate. The reaction mixture can be filtered, to remove the mercuric or cupric sulfide by-product, and the filtrate can be concentrated to give compounds 10 in crude form. Compounds 10 can be recrystallized as the free base or converted to an acid-addition salt by conventional reaction with a suitable acid. In certain cases, cyclization can be affected by simply refluxing the thioureas 35 in a suitable organic solvent, e.g., methanol, in the absence of mercuric or cupric oxide.

Quinoxalines 15 can be synthesized by well-known synthetic procedures, for example, procedures disclosed in J. A. JOULE ET AL., HETEROCYCLIC CHEMISTRY 189-224 (3rd ed. 1995), hereby incorporated herein by reference.

Topical Formulations of the Invention

In certain aspects, compounds of the present teachings can be delivered to the affected area of the skin in a pharmaceutically acceptable topical carrier. As used herein, a pharmaceutically acceptable topical carrier can be any pharmaceutically acceptable formulation that can be applied to the skin surface for topical, dermal, intradermal, or transdermal delivery of a pharmaceutical or medicament. The combination of a pharmaceutically acceptable topical carrier and a compound of the invention is termed a topical formulation of the invention. Topical formulations of the invention can be prepared by mixing a compound of the invention with a topical carrier according to well-known methods in the art, for example, methods provided by standard reference texts such as, REMINGTON: THE SCIENCE AND PRACTICE OF PHARMACY 1577-1591, 1672-1673, 866-885 (Alfonso R. Gennaro ed. 19th ed. 1995); Ghosh, T. K.; et al. TRANSDERMAL AND TOPICAL DRUG DELIVERY SYSTEMS (1997), both of which are hereby incorporated herein by reference.

A topical carrier useful for topical delivery of compounds of the invention can be any carrier known in the art for topically administered pharmaceuticals, for example, but not limited to, pharmaceutically acceptable solvents, such as a polyalcohol or water; emulsions (either oil-in-water or water-in-oil emulsions), such as creams or lotions; micro emulsions; gels; ointments; liposomes; powders; and aqueous solutions or suspensions, such as standard ophthalmic preparations.

Emulsions, Gels, and Ointments as Topical Carriers

In some embodiments, a topical carrier used to deliver a compound of the invention can be an emulsion, gel, or ointment. Emulsions, such as creams and lotions are suitable topical formulations for use in the invention. An emulsion, as used herein, is defined as a dispersed system comprising at least two immiscible phases, one phase dispersed in the other as droplets ranging in diameter from about 0.1 micron to about 100 microns. An emulsifying agent can be included to improve stability. When water is the dispersed phase and an oil is the dispersion medium, the emulsion is termed a water-in-oil emulsion. When an oil is dispersed as droplets throughout the aqueous phase as droplets, the emulsion is termed an oil-in-water emulsion. Emulsions, such as creams and lotions that can be used as topical carriers and their preparation are disclosed in REMINGTON: THE SCIENCE AND PRACTICE OF PHARMACY 282-291 (Alfonso R. Gennaro ed. 19th ed. 1995), hereby incorporated herein by reference.

In another aspect, a topical carrier used to deliver a compound of the invention can be a gel, for example, a two-phase gel or a single-phase gel. Gels are defined herein as semisolid systems consisting of suspensions of small inorganic particles or large organic molecules interpenetrated by a liquid. When the gel mass comprises a network of small discrete inorganic particles, it is classified as a two-phase gel. Single-phase gels consist of organic macromolecules distributed uniformly throughout a liquid such that no apparent boundaries exist between the dispersed macromolecules and the liquid. Suitable gels for use in the invention are disclosed in REMINGTON: THE SCIENCE AND PRACTICE OF PHARMACY 1517-1518 (Alfonso R. Gennaro ed. 19th ed. 1995), hereby incorporated herein by reference. Other suitable gels are disclosed in U.S. Pat. No. 6,387,383 (issued May 14, 2002); U.S. Pat. No. 6,517,847 (issued Feb. 11, 2003); and U.S. Pat. No. 6,468,989 (issued Oct. 22, 2002), each of which patents is hereby incorporated herein by reference.

Polymer thickeners (gelling agents) that may be used include those known to skilled artisans. Non-limiting examples of polymer thickeners include hydrophilic and hydroalcoholic gelling agents frequently used in the cosmetic and pharmaceutical industries. Some non-limiting examples of hydrophilic or hydroalcoholic gelling agent include "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). In some aspects, the gelling agent can comprise between about 0.2% to about 4% by weight of the composition, i.e., w/w. More particularly, the compositional weight percent range for "CARBOPOL®" can be between about 0.5% w/w to about 2% w/w, while the weight percent range for "NATROLSOL®" and "KLUCEL®" can be between about 0.5% to about 4%. In various configurations, the compositional weight percent range for both "HYPAN®" and "STABILEZE®" can be between 0.5% w/w to about 4% w/w.

"CARBOPOL®" is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other examples of gelling polymers include hydroxyethylcellulose, cellulose gum, MVE/MA decadiene crosspolymer, PVM/MA copolymer, or combinations thereof.

In another embodiment, a topical carrier used to deliver can be an ointment. Ointments are defined herein as oleaginous semisolids that contain little if any water. An ointment can be hydrocarbon based, such as a wax, petrolatum, or gelled mineral oil. Suitable ointments for use in the invention are well known in the art and are disclosed in REMINGTON: THE SCIENCE AND PRACTICE OF PHARMACY 1585-1591 (Alfonso R. Gennaro ed. 19th ed. 1995), hereby incorporated herein by reference.

Aqueous Topical Formulations

In another embodiment, a topical carrier used in the topical formulations can be an aqueous solution or suspension. Well-known ophthalmic solutions and suspensions can be suitable topical carriers. Examples of suitable aqueous topical formulations are described in REMINGTON: THE SCIENCE AND PRACTICE OF PHARMACY 1563-1576 (Alfonso R. Gennaro ed. 19th ed. 1995), hereby incorporated herein by reference. Other examples of suitable aqueous topical carrier systems are disclosed in U.S. Pat. No. 5,424,078 (issued Jun. 13, 1995); U.S. Pat. No. 5,736,165 (issued Apr. 7, 1998); U.S. Pat. No. 6,194,415 (issued Feb. 27, 2001); U.S. Pat. No. 6,248,741 (issued Jun. 19, 2001); U.S. Pat. No. 6,465,464 (issued Oct. 15, 2002), all of which patents are hereby incorporated herein by reference.

In various aspects, the pH of an aqueous topical formulation can be within the range of from about 6 to about 8, or from about 6.3 to about 6.5. To stabilize the pH, an effective amount of a buffer can be included. In some embodiments, a buffering agent can be present in an aqueous topical formulation in an amount of from about 0.05% w/w to about 1% w/w. Acids or bases can be used to adjust the pH as needed. Non-limiting examples of buffering agents include acetate buffers, citrate buffers, phosphate buffers, lactic acid buffers, and borate buffers.

Tonicity-adjusting agents can be included in aqueous topical formulations of the present teachings. Examples of suitable tonicity-adjusting agents include, but are not limited to, sodium chloride, potassium chloride, mannitol, dextrose, glycerin, and propylene glycol. The amount of the tonicity agent can vary widely depending on the formulation's desired properties. In one embodiment, the tonicity-adjusting agent is present in the aqueous topical formulation in an amount of from about 0.5% w/w to about 0.95% w/w.

In some aspects, aqueous topical formulations can have a viscosity in the range of from about 15 cps to about 25 cps. The viscosity of aqueous solutions of the invention can be adjusted by adding viscosity adjusting agents, for example, but not limited to, polyvinyl alcohol, povidone, hydroxypropyl methyl cellulose, poloxamers, carboxymethyl cellulose, or hydroxyethyl cellulose.

In certain embodiments, an aqueous topical formulation can be isotonic saline comprising a preservative, such as benzalkonium chloride or chlorine dioxide, a viscosity-adjusting agent, such as polyvinyl alcohol, and a buffer system such as sodium citrate and citric acid.

Excipients

Topical formulations of the present teachings can comprise pharmaceutically acceptable excipients such as those listed in REMINGTON: THE SCIENCE AND PRACTICE OF PHARMACY 866-885 (Alfonso R. Gennaro ed. 19th ed. 1995; Ghosh, T. K.; et al. TRANSDERMAL AND TOPICAL DRUG DELIVERY SYSTEMS (1997), hereby incorporated herein by reference, and can include, without limitation, protectives, adsorbents, demulcents, emollients, preservatives, antioxidants, moisturizers, buffering agents, solubilizing agents, skin-penetration agents, and surfactants.

Suitable protectives and adsorbents include, but are not limited to, dusting powders, zinc sterate, collodion, dimethicone, silicones, zinc carbonate, aloe vera gel and other aloe products, vitamin E oil, allatoin, glycerin, petrolatum, and zinc oxide.

Suitable demulcents include, but are not limited to, benzoin, hydroxypropyl cellulose, hydroxypropyl methylcellulose, and polyvinyl alcohol.

Suitable emollients include, but are not limited to, animal and vegetable fats and oils, myristyl alcohol, alum, and aluminum acetate.

Suitable preservatives include, but are not limited to, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other antimicrobial agents such as chlorhexidine, chlorocresol, benzoic acid and polymyxin.

Chlorine dioxide ($ClO_2$), preferably, stabilized chlorine dioxide, can be used as a preservative for use with topical formulations of the invention. The term "stabilized chlorine dioxide" is well known in the industry and by those skilled in the art. Stabilized chlorine dioxide includes one or more chlorine dioxide precursors such as one or more chlorine dioxide-containing complexes and/or one or more chlorite-containing components and/or one or more other entities capable of decomposing or being decomposed in an aqueous medium to form chlorine dioxide. U.S. Pat. No. 5,424,078 (issued Jun. 13, 1995), hereby incorporated herein by reference, discloses a form of stabilized chlorine dioxide and a method for producing same, which can be used as a preservative for aqueous ophthalmic solutions and is useful in topical formulations of the invention. The manufacture or production of certain stabilized chlorine dioxide products is described in U.S. Pat. No. 3,278,447, hereby incorporated herein by reference. A commercially available stabilized chlorine dioxide which can be utilized in the practice of the present invention is the proprietary stabilized chlorine dioxide of BioCide International, Inc. of Norman, Okla., sold under the trademark Purogene™ or Purite™ Other suitable stabilized chlorine dioxide products include that sold under the trademark DURAKLOR by Rio Linda Chemical Company, Inc., and that sold under the trademark Antheium Dioxide by International Dioxide, Inc.

Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerin, sorbitol, polyethylene glycols, urea, and propylene glycol.

Suitable buffering agents for use with the invention include, but are not limited to, acetate buffers, citrate buffers, phosphate buffers, lactic acid buffers, and borate buffers.

Suitable solubilizing agents include, but are not limited to, quaternary ammonium chlorides, cyclodextrins, benzyl benzoate, lecithin, and polysorbates.

Suitable skin-penetration agents include, but are not limited to, ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methylpyrrolidone.

Pharmaceutical Additives

Topical formulations of the present teachings can include pharmaceutical compounds or their pharmaceutically acceptable salts, for example, but not limited to, topical corticosteroids and other anti-inflammatory agents, such as betamethasone, diflorasone, amcinonide, fluocinolone, mometasone, hydrocortisone, prednisone, and triamcinolone; local anesthetics and analgesics, such as camphor, menthol, lidocaine, and dibucaine, and pramoxine; antifungals, such as ciclopirox, chloroxylenol, triacetin, sulconazole, nystatin, undecylenic acid, tolnaftate, miconizole, clotrimazole, oxiconazole, griseofulvin, econazole, ketoconazole, and amphotericin B; antibiotics and anti-infectives, such as mupirocin, erythromycin, clindamycin, gentamicin, polymyxin, bacitracin, and silver sulfadiazine; and antiseptics, such as iodine, povidine-iodine, benzalkonium chloride, benzoic acid, chlorhexidine, nitrofurazine, benzoyl peroxide, hydrogen peroxide, hexachlorophene, phenol, resorcinol, and cetylpyridinium chloride.

Dosage

Dosages and dosing frequency can be determined by a skilled artisan such as a trained medical professional. Dosage can depend on the activity of an $\alpha_2$ adrenergic receptor agonist, the characteristics of the particular topical formulation, and the identity and severity of the dermatologic disorder treated or prevented.

In general, a compound of the invention can be present in a formulation in an amount of from about 0.01% w/w to about 5% w/w, preferably, of from about 0.05 percent to about 1 percent, more preferably, of from about 0.1 percent to about 0.2 percent of the total weight of the formulation.

Topical Administration

Generally the amount of a topical formulation applied to an affected skin area ranges from about 0.1 g/cm$^2$ to about 5 g/cm$^2$ of skin surface area, from about 0.2 g/cm$^2$ to about 0.5 g/cm$^2$ of skin surface area.

To promote skin tightening, the topical formulations of the invention are topically applied directly to the skin in an affected area in any conventional manner well known in the art. As used herein, "ameliorating skin sagging, creasing and/or wrinkling" and "promoting skin tightening" include lessening the severity of skin sagging, creasing and/or wrinkling, or preventing their appearance. Lessening severity of skin sagging, creasing and/or wrinkling can include complete or partial reversal of skin sagging, creasing and/or wrinkling.

In various aspects, a composition of the present teachings can be topically applied by any known method in the art, for example, with the aid of a dropper or applicator stick, as a mist via an aerosol applicator, via an intradermal or transdermal patch, or by simply spreading a formulation of the invention onto the affected area with fingers. Typically, an application of a topical composition can noticeably ameliorate skin sagging, creasing and/or wrinkling within minutes following application. Results differ from patient to patient. The effects are preferably seen within about eight minutes, even more preferably within about five minutes, most preferably within about two minutes, and optimally immediately after application of the topical administration.

A composition can be maximally effective at about 30 minutes after application, and the ameliorative effects can last up to about 8 hours, up to about 12 hours, up to about 18 hours, or up to about 24 hours. Accordingly, in some aspects, a composition can be topically applied to skin at a site of skin sagging, creasing and/or wrinkling once per day, twice per day, or three times per day.

Use of Topical Formulations of the Invention in Combination with Other Skin-Disorder Treatments The formulations of the invention can be used in combination with other treatments and medications to provide more effective treatment or prevention of skin sagging, creasing and/or wrinkling. In a preferred embodiment, topical formulations can be used in combination with treatment regimens and medications well known for treatment of dermatologic disorders, such as those disclosed in THE MERCK MANUAL 811-830 (Keryn A. G. Lane et al. eds. 17th ed. 2001), hereby incorporated herein by reference.

In some aspects, a formulation, composition or compound can be used in combination with another medicament or treatment. In some configurations, a combination can be administered to a subject in a sequence and within a time interval such that they can act together to treat or prevent skin sagging, creasing and/or wrinkling.

Any suitable route of administration can be employed to deliver the additional treatment or medication including, but not limited to, oral, intraoral, rectal, parenteral, topical, epicutaneous, transdermal, subcutaneous, intramuscular, intranasal, sublingual, buccal, intradural, intraocular, intrarespiratory, or nasal inhalation.

In one embodiment, the topical formulations can be used in combination with systemic administration of antibiotics or retinoids including, but not limited to, orally dosed antibiotics, such as tetracycline, minocin, minocycline, erythromycin, and doxycycline, and orally dosed retinoids such as isotretinoins (e.g., ACCUTANE or ROACCUTANCE).

In other embodiments, the topical formulations disclosed herein can be used in combination with other topical treatments including, but not limited to, topical formulations consisting of metronidazole, hydrogen peroxide, benzoyl peroxide, lipoic acid, and azelaic acid, and sulfur preparations; topically dosed antibiotics, such as metronidazole, clindamycin, and erythromycin; topical retinoids such as tretinoin, adapalene, tazarotene; or topical steroids.

In other embodiments, topical formulations described herein can be used in combination with other therapies such as, for example, mixed light pulse therapy (photoderm), pulsed dye laser treatment, or electrosurgery.

Article of Manufacture

Certain aspects of the present teachings include an article of manufacture which comprises a topical formulation in a suitable container with labeling and instructions for use. The container can be, in non-limiting example, a dropper or tube with a suitable small orifice size, such as an extended tip tube made of any pharmaceutically suitable material.

A topical formulation can be filled and packaged into a plastic squeeze bottle or tube. Suitable container-closure systems for packaging topical formulations of the invention are commercially available for example, from Wheaton Plastic Products, 1101 Wheaton Avenue, Millville, N.J. 08332.

In some configurations, a formulation can be packaged with written material, such as, for example, instructions, a pamphlet or a package label. The labeling instructions explain how to administer topical formulations of the invention, in an amount and for a period of time sufficient to treat or prevent skin sagging, creasing and/or wrinkling. The labeling instructions can be an important aspect in that before a composition can be approved for any particular use, it may require approval for marketing by the United States Food and Drug Administration. Part of that process includes providing a label that will accompany the pharmaceutical composition that is ultimately sold. Accordingly, a label can include dosage and administration instructions, the topical formulation's composition, the clinical pharmacology, drug resistance, pharmacokinetics, absorption, bioavailability, and contraindications.

EXAMPLES

The following examples are provided for illustrative purposes only and are not to be construed as limiting the invention's scope in any manner. The description of an article, a composition, or a method in an example does not imply that the described article or composition has, or has not, been produced, or that that the described method has, or has not, been performed, regardless of verb tense.

Example 1

Synthesis of (5-Bromo-quinoxalin-6-yl)-(4,5-dihydro-1H-imidazol-2-yl)-amine

To a stirred solution of 6-amino-5-bromoquinoxaline hydrobromide (10 g) in distilled water (150 ml) is added thiophosgene (3 ml). The solution is stirred for two hours at room temperature and the resultant precipitate is collected by filtration, washed with water, and dried to afford 5-bromo-6-isothiocyanato-quinoxaline.

The 5-bromo-6-isothiocyanato-quinoxaline (3.5 g.) is directly dissolved in benzene (400 ml) and added dropwise to a well-stirred solution of ethylene diamine (15 g.) in benzene (50 ml). During a period of about two hours, an oil separates as a lower layer. The upper benzene layer is poured off and the oil is washed with diethyl ether and then dissolved in methanol (500 ml). The methanolic solution is refluxed until hydrogen sulfide evolution ceases. The methanolic solution is concentrated in vacuo to a volume of approximately 100 ml upon which a yellow solid precipitates. The precipitate is collected by filtration and recrystallized from methanol to afford of (5-Bromo-quinoxalin-6-yl)-(4,5-dihydro-1H-imidazol-2-yl)-amine: m.p. 250-251 C.

Example 2

An aqueous solution topical formulation of the invention comprises (5-Bromo-quinoxalin-6-yl)-(4,5-dihydro-1H-imidazol-2-yl)-amine-L-tartrate (brimonidine tartrate) (0.15% w/w); Puriteg (0.005% w/w) (stabilized chlorine dioxide) as a preservative; and the inactive ingredients: boric acid; calcium chloride; magnesium chloride; potassium chloride; purified water; sodium borate; sodium carboxymethylcellulose; sodium chloride; with hydrochloric acid and/or sodium hydroxide to adjust the pH to 5.6 to 6.6. The osmolality is in the range of 250-350 mOsmol/kg.

Example 3

An aqueous solution topical formulation comprises (5-Bromo-quinoxalin-6-yl)-(4,5-dihydro-1H-imidazol-2-yl)-amine-L-tartrate, (brimonidine tartrate) (0.15% w/w); benzalkonium chloride (0.005 wt. %) as a preservative; and the inactive ingredients: boric acid; calcium chloride; magnesium chloride; potassium chloride; purified water; sodium borate; sodium carboxymethylcellulose; sodium chloride; with hydrochloric acid and/or sodium hydroxide to adjust the pH to 5.6 to 6.6. The osmolality is in the range of 250-350 mOsmol/kg.

Example 4

A cream topical formulation is described in the Table below.

TABLE 2

Cream Topical Formulation (Hydrophilic Ointment)

| Ingredient | Weight Percent |
|---|---|
| Brimonidine tartrate | 0.15% |
| Stearic acid | 7% |
| Stearyl alcohol | 5% Cetyl alcohol |
| 2% Glycerin | 10% |
| Sodium lauryl sulfate | 1% |
| Propylparaben | 0.05% |
| Methylparaben | 0.25% |
| Disodium edetate | 0.055 |
| Distilled water | QS |

To make the formulation, the stearyl alcohol and the white petrolatum were melted on a steam bath, and warmed to about 75 degrees C. The other ingredients, previously dissolved in the water and warmed to 75 degrees C., were then added, and the mixture was stirred until it congealed. The mixture was then allowed to cool with stirring, and brimonidine tartrate was then added as a concentrated solution.

Example 5

An ointment topical formulation is described in the Table below.

TABLE 3

Ointment Formulation (Hydrophilic Ointment)

| Ingredients | Weight |
|---|---|
| Brimonidine tartrate | 10 g |
| Cholesterol | 30 g |
| Stearyl Alcohol | 30 g |
| White Wax | 80 g |
| White Petrolatum | 850 g |

To make the formulation, the stearyl alcohol and white wax were mixed together on a steam bath. The cholesterol was then added and stirred until it completely dissolved. The white petrolatum was then added and mixed. The mixture was removed from the bath, and stirred until it congealed. With continuous stirring, brimonidine tartrate was added as a concentrated slurry.

Example 6

A gel formulation is described in the table below.

TABLE 4

Gel Formulation

| Ingredients | Weight % |
|---|---|
| Brimonidine tartrate | 1.0% |
| Methylparaben NF | 0.15% |
| Propylparaben NF | 0.03% |
| Hydroxyethylcellulose NF | 1.25% |
| Disodium Edetate USP | 0.05% |
| Purified Water, USP | QS 100% |

Example 7

A gel formulation is described in the Table below.

TABLE 5

Gel Formulation

| Ingredients | Weight % |
|---|---|
| Brimonidine tartrate | 1.0% |
| Methylparaben | 0.20% |

TABLE 5-continued

Gel Formulation

| Ingredients | Weight % |
| --- | --- |
| Propylparaben | 0.05% |
| Carbomer 934P NF | 1.0% |
| Sodium Hydroxide | QS pH 7 |
| Purified Water USP | QS 100% |

The ingredients are mixed together and aqueous sodium hydroxide is slowly added to the mixture until a pH of about 7 is reached and the gel is formed.

Example 8

A gel formulation is described in the Table below.

TABLE 6

Gel Formulation

| Ingredients | Weight % |
| --- | --- |
| Brimonidine tartrate | 1.0% |
| Methylparaben | 0.2% |
| Propylparaben | 0.05% |
| "CARBOPOL ®" | 1.0% |
| Triethanolamine | QS pH 7 |
| Water | QS 100% |

The ingredients are mixed together and stirred. Triethanolamine is added until a pH of about 7 is attained.

Example 9

A foam formulation is described in Table 7 below.

TABLE 7

Foam Formulation

| Ingredients | Amount (Weight %) |
| --- | --- |
| Brimonidine tartrate | 0.2 |
| Stearic Acid | 4.2 |
| Laureth-23 | 1.4 |
| Sodium Lauryl Sulfate | 0.5 |
| Triethanolamine | 2.2 |
| Butylated hydroxytoluene (BHT) | 0.01 |
| Fragrance | 0.5 |
| Aeron A-31 Propellant | 3 |
| Water | 87.99 |

The water is heated to 80-85° C., after which stearic acid is added. Once the stearic acid is melted, the laureth-23 is added, melted, and mixed well. Next, triethanolamine is added and the resulting composition is mixed well for about 30 minutes to form a soap. The resulting soap is then cooled to about 65° C., after which sodium lauryl sulfate is added. The composition is then mixed well. Next, the BHT and the Brimonidine tartrate are added, followed by mixing. The resulting composition is then cooled to room temperature and the fragrance added. The product is packaged with the Aeron A-31 propellant in an aerosol can using conventional techniques and mechanically shaken for 5 minutes. The product dispenses as a cone-shaped spray that deposits onto the skin as a layer of rich lather that quickly covers a wide area of skin.

Examples 10-13

Additional foam formulations are described in Table 8 below.

TABLE 8

Foam Formulations

| | Amount (Weight %) | | | |
| --- | --- | --- | --- | --- |
| Ingredients | Example 10 | Example 11 | Example 12 | Example 13 |
| Brimonidine tartrate | 0.1 | 0.15 | 0.2 | 0.25 |
| Stearic Acid | 6.3 | 5.0 | 3.6 | 3.1 |
| Laureth-23 | 2.1 | 1.7 | 1.2 | 1.0 |
| Sodium Lauryl Sulfate | 0.8 | 0.6 | 0.5 | 0.4 |
| Triethanolamine | 3.2 | 2.6 | 1.9 | 1.6 |
| Butylated hydroxytoluene (BHT) | 0.02 | 0.02 | 0.01 | 0.01 |
| Fragrance | 0.5 | 0.5 | 0.5 | 0.5 |
| Aeron A-31 Propellant | 3 | 3 | 3 | 3 |
| Water | 83.98 | 86.43 | 89.09 | 90.14 |

Preparation: these foam formulations are prepared and packaged as in Example 9. The product dispenses as a cone-shaped spray that deposits onto the skin as a layer of rich lather that quickly covers a wide area of skin.

Example 14

An additional foam formulation is described in Table 9 below.

TABLE 9

Foam Formulation

| Ingredient | Amount (Weight %) |
| --- | --- |
| Brimonidine tartrate | 0.2 |
| Water | 91.11 |
| Palmitic Acid | 2.12 |
| Laureth-23 | 0.93 |
| Triethanolamine (99%) | 1.13 |
| Cetyl Dimethicone Copolyol | 0.19 |
| Mineral Oil | 0.31 |
| Stearyl Alcohol | 0.31 |
| Lauramide DEA | 0.15 |
| PEG-150 Distearate | 0.05 |
| Imidazolidinyl Urea | 0.0016 |
| Methylparaben | 0.0005 |
| Propylparaben | 0.00003 |
| Freeze Dried Aloe Powder | 0.0015 |
| Fragrance | 0.50 |
| Aeron A-31 Propellant | 3.00 |

The aqueous phase is prepared as follows. The water is heated to 80° C., after which palmitic acid is added. Once the palmitic acid is melted, the laureth-23 is added, melted, and mixed well. Next, triethanolamine is added and the resulting composition is mixed well for about 15 minutes to form a soap.

Stearyl alcohol, mineral oil, lauramide DEA, cetyl dimethicone copolyol, PEG-150 distearate, and BHT are mixed and heated at 55° C. to form the oil phase. The oil phase is combined with the aqueous phase at 80° C. and mixed well for about 15 minutes. The resulting mixture is then cooled to room temperature and the imidazolidinyl urea, methylparaben, and propylparaben are added, and then mixed well. The brimonidine tartrate is then added, and mixed well. Next, the fragrance is added, followed by gentle mixing. The aloe is then dissolved in make-up water and added with slow mixing to form the product formulation which is then packaged in an aerosol can as described in Example 9.

The product dispenses as a cone-shaped spray that deposits onto the skin as a layer of rich lather that quickly covers a wide area of skin.

Example 15

An additional, non-soapy foam formulation is described in Table 10 below.

TABLE 10

Foam Formulation

| Ingredient | Amount (Weight %) |
| --- | --- |
| Brimonidine tartrate | 0.2 |
| Ethanol | 6 |
| Ethyl Ester of PVM/MA | 4 |
| Copolymer Dimethicone Copolyol | 0.1 |
| Water | 80.37 |
| PVP/VA Copolymer | 1 |
| Sodium Lauryl Sulfate | 1 |
| Oleth-20 | 0.5 |
| Cocamide MEA | 0.05 |
| Methyl Paraben | 0.1 |
| Aminomethyl Propanol | 0.53 |
| Stearalkonium Chloride | 0.05 |
| Steareth-16 | 0.1 |
| Panthenol | 0.5 |
| Fragrance | 0.5 |
| Aeron A-46 | 5 |

The alcohol phase is prepared by dissolving ethyl ester of PVM/MA copolymer in ethanol, after which dimethicone is added and mixed well. The aqueous phase is prepared by heating the water to 65° C., after which the PVP/VA copolymer is added and mixed well. The oil phase is prepared by mixing the oleth-20, cocamide MEA, and steareth-16 at 60° C. to form a blend. The oil phase is then added to the aqueous phase at 65° C. and mixed well. Next, the methylparaben is added to the mixture, followed by mixing, after which the aminomethyl propanol, stearalkonium chloride, and panthenol are added and mixed until uniform. The resulting composition is cooled to room temperature, after which the alcohol phase is added and mixed well. The fragrance is then added and mixed gently to form the product. The product is then packaged in an aerosol can.

The product dispenses as a cone-shaped spray that deposits onto the skin as a layer of rich lather that quickly covers a wide area of skin.

Example 16

Use of Oxymetazoline

An oxymetazoline solution (Afrin®, 0.05% solution, Schering-Plough HealthCare Products) is placed onto a cotton tipped swab and applied to approximately 4 cm$^2$ of naso-facial skin displaying skin sagging, creasing and/or wrinkling.

Example 17

Use of Epinephrine

An epinephrine solution (Epipen®, trademark of Dey®, L.P.) containing approximately 0.3 mg of epinephrine is placed in a glass container. The solution is placed onto a cotton tipped swab and then applied to approximately 4 cm$^2$ of naso-facial skin displaying skin sagging, creasing and/or wrinkling.

Example 18

A middle-aged woman has severe wrinkling on her face. She applies 0.2% COL-118 (an α2 adrenergic receptor agonist supplied by CollaGenex Pharmaceuticals, Inc., Newtown, Pa.). Wrinkling is noticeably diminished within 5 minutes by casual observation. After about 10 minutes, nearly all the wrinkles are gone. The effect lasts at least 8 hr.

DEFINITIONS

As used herein, the term "prodrug" refers to a drug precursor which is inactive but can be activated by a biological or biochemical process, such as, for example, enzymatic hydrolysis.

The phrase "pharmaceutically acceptable salt(s)", as used herein, means those salts of compounds of the invention that are safe and effective for topical use in mammals and that possess the desired biological activity. Pharmaceutically acceptable salts include salts of acidic or basic groups present in compounds of the present teachings. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds disclosed herein can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

The term "pharmaceutically acceptable topical formulation" as used herein means any formulation which is pharmaceutically acceptable for topical delivery of a compound. A "topical formulation" can comprise at least a compound of the present disclosure. The choice of topical formulation will depend on several factors, including the nature of the symptoms to be treated or prevented, the physiochemical characteristics of the particular compound of the invention and of other excipients present, their stability in the formulation, available manufacturing equipment, and cost constraints.

As used herein, a "therapeutically effective amount" of a compound means the an amount of the compound that is effective to treat or prevent skin sagging, creasing and/or wrinkling.

As used herein, the term "subject" means any animal, preferably a mammal, to which will be or has been administered compounds or topical formulations of the present teachings. The term "mammal" as used herein, encompasses any mammal. Examples of mammals include, but are not limited to, cows, horses, sheep, pigs, cats, dogs, mice, rats, rabbits, guinea pigs, monkeys, humans etc.

The term "analog" refers to a chemical compound that is structurally similar to a parent compound and has chemical properties or pharmaceutical activity in common with the parent compound. Analogs include, but are not limited to, homologs, i.e., where the analog differs from the parent compound by one or more carbon atoms in series; positional isomers; compounds that differ by interchange of one or more atoms by a different atom, for example, replacement of a carbon atom with an oxygen, sulfur, or nitrogen atom; and compounds that differ in the identity of one or more functional groups, for example, the parent compound differs from its analog by the presence or absence of one or more suitable substituents. Suitable substituents include, but are not limited to, $(C_1-C_8)$alkyl; $(C_1-C_8)$alkenyl; $(C_1-C_8)$alkynyl: aryl; $(C_2-C_5)$heteroaryl; $(C_1-C_6)$heterocycloalkyl; $(C_3-C_7)$cycloalkyl; O—$(C_1-C_8)$alkyl; O—$(C_1-C_8)$alkenyl; O—$(C_1-C_8)$alkynyl; O-aryl; CN; OH; oxo; halo, C(O)OH; COhalo; O(CO)halo; $CF_3$, $N_3$; $NO_2$, $NH_2$; NH(($C_1-C_8$)alkyl); N(($C_1-C_8$)alkyl)$_2$; NH(aryl); N(aryl)$_2$N(($C_1-C_8$)alkyl)(aryl); (CO)$NH_2$; (CO)NH(($C_1-C_8$)alkyl); (CO)N(($C_1-C_8$)alkyl)$_2$; (CO)NH(aryl); (CO)N(aryl)$_2$; O(CO)$NH_2$; NHOH; NOH(($C_1-C_8$)alkyl); NOH(aryl); O(CO)NH(($C_1-C_8$)alkyl); O(CO)N(($C_1-C_8$)alkyl-)$_2$; O(CO)NH(aryl); O(CO)N(aryl)$_2$; CHO; CO(($C_1-C_8$)alkyl-); CO(aryl); C(O)O(($C_1-C_8$)alkyl); C(O)O(aryl); O(CO)(($C_1-C_8$)alkyl); O(CO)(aryl); O(CO)O(($C_1-C_8$)alkyl-); O(CO)O(aryl); S—$(C_1-C_8)$alkyl; S—$(C_1-C_8)$alkenyl; S—$(C_1-C_8)$alkynyl; S-aryl; S(O)$C_1-C_8$)alkyl; S(O)—$(C_1-C_8)$alkenyl; S(O)—$(C_1-C_8)$alkynyl; and S(O)-aryl; S(O)$_2$—$(C_1-C_8)$alkyl; S(O)$_2$—$(C_1$—C.sub-0.8)alkenyl; S(O)$_2$—$(C_1-C_8)$alkynyl; and S(O)$_2$-aryl. One of skill in the art can readily choose a suitable substituent based upon the stability and pharmacological activity of a compound.

The term "alkyl" means a saturated, monovalent, unbranched or branched hydrocarbon chain. Examples of alkyl groups include, but are not limited to, $(C_1-C_3)$alkyl groups, such as methyl, ethyl, propyl, isopropyl and $(C_4-C_8)$ alkyl groups, such as 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, heptyl, and octyl. An alkyl group can be unsubstituted or substituted with one or two suitable attachments.

The term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to $(C_2-C_8)$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "alkynyl" means monovalent, unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_8)$alkynyl groups, such as ethynyl, propynyl, butynyl, pentynyl, hexynyl, methylpropynyl, 4-methyl-1-butynyl, 4-propyl-2-pentynyl-, and 4-butyl-2-hexynyl. An alkynyl group can be unsubstituted or substituted with one or two suitable substituents.

The term "aryl" means a monocyclic or polycyclic-aromatic group comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. Preferably, the aryl group is a monocyclic ring, wherein the ring comprises 6 carbon atoms, referred to herein as "$(C_6)$aryl".

The term "heteroaryl" means a monocyclic- or polycyclic aromatic ring comprising carbon atoms, hydrogen atoms, and one or more heteroatoms, preferably, 1 to 3 heteroatoms, independently selected from nitrogen, oxygen, and sulfur. As is well known to those skilled in the art, heteroaryl rings have less aromatic character than their all-carbon counterparts. Thus, for the purposes of the invention, a heteroaryl group need only have some degree of aromatic character. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, phenyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "$(C_2-C_5)$heteroaryl".

The term "cycloalkyl" means a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes and $(C_3-C_7)$cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two suitable substituents. Preferably, the cycloalkyl group is a monocyclic ring or bicyclic ring.

The term "heterocycloalkyl" means a non-aromatic monocyclic or polycyclic ring comprising carbon and hydrogen atoms and at least one heteroatom, preferably, 1 to 4 heteroatoms selected from nitrogen, oxygen, and sulfur. A heterocycloalkyl group can have one or more carbon-carbon double bonds or carbon-heteroatoms double bonds in the ring as long as the ring is not rendered aromatic by their presence. Examples of heterocycloalkyl groups include aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 2 to 6 carbon atoms and from 1 to 3 heteroatoms, referred to herein as $(C_1-C_6)$heterocycloalkyl.

The term "halogen" encompasses fluorine, chlorine, bromine, and iodine. Correspondingly, the term "halo" means fluoro, chloro, bromo, and iodo.

In one embodiment, "reducing" refers to an amelioration, prophylaxis, or reversal of a disease or disorder, or at least one discernible symptom thereof, for example, reducing skin sagging, creasing and/or wrinkling. In another embodiment, "reducing" refers to an amelioration, prophylaxis, or reversal of at least one measurable physical parameter related to skin sagging, creasing and/or wrinkling, not necessarily discernible in or by the mammal. In yet another embodiment, "reducing" refers to inhibiting or slowing the progression of a disease or disorder, either physically, e.g., stabilization of a discernible symptom, physiologically, e.g., stabilization of a physical parameter, or both. In yet another embodiment, "reducing" refers to delaying the onset of a disease or disorder.

In certain embodiments, the compounds of the invention can be administered as a preventative measure. As used herein, "prevention" or "preventing" refers to a reduction of the risk of acquiring a given disease or disorder. In a preferred mode of the embodiment, the compounds of the invention are administered as a preventative measure to a subject having a predisposition to skin sagging, creasing and/or wrinkling even though symptoms of the disorder are absent or minimal.

As used herein, "carbomer" is the USP designation for various polymeric acids that are dispersible but insoluble in water. When the acid dispersion is neutralized with a base a clear, stable gel is formed. Carbomer 934P is physiologically inert and is not a primary irritant or sensitizer. Other carbomers include 910, 940, 941, and 1342.

In view of the above Background, Summary, Figures, and Detailed Description, it is clear that in certain embodiments, the present teachings disclose methods of reducing skin sagging, creasing and/or wrinkling, comprising topically administering to the skin of a subject in need of such treatment a compound of a formula:

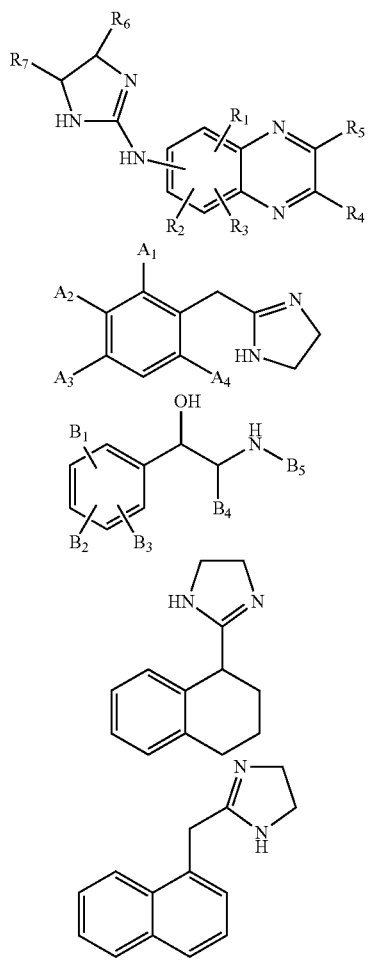

wherein each of $R_1$, $R_2$, and $R_3$ is independently hydrogen, halogen, alkyl, or alkoxy; each of $R_4$ and $R_5$ is independently hydrogen, alkyl, or alkoxy; and each of $R_6$ and $R_7$ is independently hydrogen, nitro, alkyl, or alkoxy; wherein each of $A_1$, $A_3$, and $A_4$ is independently hydrogen or alkyl; and $A_2$ is independently hydrogen or hydroxy; and wherein each of $B_1$, $B_2$, and $B_3$ is independently hydrogen, hydroxy, or alkoxy; and each of $B_4$ and $B_5$ is independently hydrogen or alkyl.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

All stereoisomers of the compounds of the instant invention are contemplated, either in admixture or in pure or substantially pure form. The definition of compounds according to the invention embraces all the possible stereoisomers and their mixtures; it also embraces the racemic forms and the isolated optical isomers having the specified activity. The racemic forms can be resolved by physical methods, such as, for example, fractional crystallization, separation, or crystallization of diastereomeric derivatives or separation by chiral column chromatography. The individual optical isomers can be obtained from the racemates from the conventional methods, such as, for example, salt formation with an optically active acid followed by crystallization.

A list following the word "comprising" is inclusive or open-ended, i.e., the list may or may not include additional unrecited elements. A list following the words "consisting of" is exclusive or closed ended, i.e., the list excludes any element not specified in the list.

All numbers in the specification are approximate unless indicated otherwise.

The method of treating a condition, disorder or disease with a chemical compound or a chemical composition includes the use of the chemical compound or chemical composition in the manufacture of a medicament for the treatment of the condition, disorder or disease, i.e., Swiss type claims. A compound or a group of compounds said to be effective in treating a condition, disorder or disease includes the compound or group of compounds for use in treating the condition, disorder or disease.

One of ordinary skill in the art can make many variations and modifications to the above-described embodiments of the invention without departing from the spirit or scope of the appended claims. Accordingly, all such variations and modifications are within the scope of the appended claims.

The term "group consisting of" is equivalent to the term "group including."

What is claimed is:

1. A method of reducing skin sagging, creasing and/or wrinkling, the method comprising topically administering to the sagging, creasing, and/or wrinkling skin of a person in need of treatment a composition comprising brimonidine or a pharmaceutically acceptable salt thereof, in an amount effective for amelioration of skin sagging, creasing and/or wrinkling.

2. A method of reducing skin sagging, creasing and/or wrinkling, the method comprising topically administering to the sagging, creasing, and/or wrinkling skin of a person in need of treatment the compounds shown below:

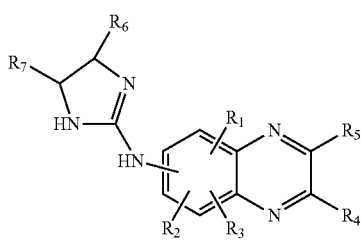

wherein each of $R_1$, $R_2$, and $R_3$ is independently hydrogen, halogen, alkyl, or alkoxy; each of $R_4$ and $R_5$ is independently hydrogen, alkyl, or alkoxy; and each of $R_6$ and $R_7$ is independently hydrogen, nitro, alkyl, or alkoxy.

3. The method according to claim 1, wherein the composition further comprises at least one pharmaceutically acceptable carrier.

4. The method according to claim 3, wherein the composition is of a form selected from the group consisting of a spray, a mist, an aerosol, a lotion, a gel, a cream, an ointment, a foam, a paste, an unguent, an emulsion, a liposomal suspension, a colloid and a combination thereof.

5. The method according to claim 3, wherein the composition further comprises a cosmetic, a foundation, a moisturizer and a sun-blocking agent.

6. The method according to claim 1, wherein the amount of composition applied to the affected area ranges from about 0.1 g/cm² to about 5 g/cm² of skin surface area.

7. The method according to claim 1, wherein the composition further comprises at least one second active ingredient selected from the group consisting of azelaic acid, benzoyl peroxide, isotretinoin, an antibiotic, a chemically modified antibiotic, a pharmaceutically acceptable salt thereof and a combination thereof, in an amount effective for amelioration of skin sagging, creasing and/or wrinkling.

8. The method according to claim 7, wherein the antibiotic is selected from the group consisting of clindamycin, doxycycline, erythromycin, metronidazole, sulfacetamide, and tetracycline.

9. The method according to claim 1, further comprising systemically administering an antibiotic in an amount effective for treatment of skin sagging, creasing and/or wrinkling.

10. The method according to claim 9, wherein the antibiotic is selected from the group consisting of clindamycin, doxycycline, erythromycin, metronidazole, sulfacetamide, and tetracycline.

11. The method according to claim 1, wherein an amount effective for amelioration of skin sagging, creasing and/or wrinkling is an amount which ameliorates skin sagging, creasing and/or wrinkling within about 5 minutes after the administering.

12. The method according to claim 1, wherein an amount effective for amelioration of skin sagging, creasing and/or wrinkling is an amount which ameliorates skin sagging, creasing and/or wrinkling for at least about 8 hours.

13. The method according to claim 12, wherein an amount effective for amelioration of skin sagging, creasing and/or wrinkling is an amount which ameliorates skin sagging, creasing and/or wrinkling for up to about 12 hours.

14. The method according to claim 12, wherein an amount effective for amelioration of skin sagging, creasing and/or wrinkling is an amount which ameliorates skin sagging, creasing and/or wrinkling for up to about 18 hours.

15. The method according to claim 12, wherein an amount effective for amelioration of skin sagging, creasing and/or wrinkling is an amount which ameliorates skin sagging, creasing and/or wrinkling for up to about 24 hours.

* * * * *